US008382854B2

(12) United States Patent
Schmenger et al.

(10) Patent No.: US 8,382,854 B2
(45) Date of Patent: Feb. 26, 2013

(54) HAIR COLORING COMPOSITIONS WITH A NON-AMMONIA ALKALIZING AGENT

(75) Inventors: Juergen Schmenger, Weiterstadt (DE); Manfred Schmitt, Bensheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/352,524

(22) Filed: Jan. 18, 2012

(65) Prior Publication Data

US 2012/0180231 A1    Jul. 19, 2012

(30) Foreign Application Priority Data

Jan. 18, 2011 (EP) .................................. 11151279

(51) Int. Cl.
*A61Q 5/10* (2006.01)
(52) U.S. Cl. ............. 8/405; 8/406; 8/431; 8/435; 8/597; 8/604
(58) Field of Classification Search ............. 8/405, 406, 8/431, 435, 597, 604
See application file for complete search history.

(56) References Cited

U.S. PATENT DOCUMENTS

| 5,480,459 | A | 1/1996 | Mager |
| 6,146,429 | A | 11/2000 | Gast |
| 6,423,101 | B1 * | 7/2002 | Yaker et al. .................. 8/405 |
| 7,186,275 | B2 | 3/2007 | Boswell |
| 2006/0248661 | A1 | 11/2006 | Wood |
| 2008/0052841 | A1 | 3/2008 | Cohen |
| 2008/0222820 | A1 | 9/2008 | Siracusa |
| 2009/0158533 | A1 | 6/2009 | Hercouet |
| 2009/0162309 | A1 | 6/2009 | Hercouet |
| 2009/0191142 | A1 | 7/2009 | Hercouet |
| 2010/0154136 | A1 | 6/2010 | Hercouet |
| 2010/0154137 | A1 | 6/2010 | Hercouet |
| 2010/0154140 | A1 | 6/2010 | Simonet |
| 2010/0154141 | A1 | 6/2010 | Hercouet |
| 2010/0154142 | A1 | 6/2010 | Audousset |
| 2010/0162492 | A1 | 7/2010 | Hercouet |
| 2010/0162493 | A1 | 7/2010 | Audousset |
| 2010/0166688 | A1 | 7/2010 | Hercouet |
| 2010/0175202 | A1 | 7/2010 | Simonet |
| 2010/0175203 | A1 | 7/2010 | Audousset |
| 2010/0175705 | A1 | 7/2010 | Hercouet |
| 2010/0175706 | A1 | 7/2010 | Hercouet |
| 2010/0178264 | A1 | 7/2010 | Hercouet |
| 2010/0186177 | A1 | 7/2010 | Hercouet |
| 2010/0199441 | A1 | 8/2010 | Hercouet |
| 2010/0223739 | A1 | 9/2010 | Hercouet |
| 2010/0247465 | A1 | 9/2010 | Simonet |
| 2011/0232667 | A1 | 9/2011 | Hercouet |
| 2012/0180230 | A1 | 7/2012 | Schmenger |

FOREIGN PATENT DOCUMENTS

| EP | 1568354 A1 | 8/2005 |
| FR | 2925308 B1 | 12/2009 |
| FR | 2940056 A1 | 6/2010 |
| FR | 2940052 B1 | 2/2011 |
| FR | 2940076 B1 | 3/2011 |
| GB | 1271331 A | 4/1972 |
| GB | 2358643 A | 8/2001 |
| JP | 2010077084 | 4/2010 |

* cited by examiner

*Primary Examiner* — Eisa Elhilo
(74) *Attorney, Agent, or Firm* — James T. Fondriest; Carl J. Roof

(57) ABSTRACT

Oxidative hair coloring compositions comprising a non-ammonia alkalizing agent, such as monoethanolamine, and hydrogen peroxide in a specific ratio. The compositions of the invention have a relatively high lift power for relatively low hair damage. The compositions may comprise little or no ammonia.

14 Claims, No Drawings

HAIR COLORING COMPOSITIONS WITH A NON-AMMONIA ALKALIZING AGENT

FIELD OF THE INVENTION

The invention relates to oxidative hair coloring compositions comprising a non-ammonia alkalizing agent, such as monoethanolamine, and hydrogen peroxide in a specific ratio. The compositions of the invention can have a relatively high lift power for relatively low hair damage. The compositions may preferably comprise little or no ammonia.

BACKGROUND OF THE INVENTION

Permanent oxidative hair coloring products have been used in professional salons and in retail products for use at home for decades. Coloring products typically comprise a tint component and an oxidizing component which are packaged separately and mixed immediately before use. The tint component contains so-called oxidative primary dyes which are small molecules (primary intermediates or couplers) and an alkalizing agent, usually ammonia. These primary dyes react with each other in the presence of an oxidizing agent to form larger, colored molecules. The tint component is thus mixed with the oxidizing component immediately prior to application to the hair to be colored and the resulting mixture is applied on hair usually for 10 to 50 nm. The oxidizing component may be for example a diluted stabilized solution of hydrogen peroxide. The mixture usually has an alkaline pH of between about 9.5 and 10.5.

Because the primary dyes are small enough to migrate into the hair shaft but the resulting colored molecules are too large to easily leave the hair, the resulting coloration is stable and undergo little fading. Furthermore, hydrogen peroxide, especially in the presence of ammonia, is capable of bleaching melanin, so that it is possible to obtain shades which are lighter or darker than the natural colour. Thus oxidative dye compositions comprising ammonia as alkalizing agent are often referred to as permanent hair colorants or "Level 3" hair colorant. Permanent hair colorants are for example marketed under the Koleston Perfect brand name by Wella Professional in Europe. Demi-permanent hair colorants, also referred to as "level 2" colorants, are also typically marketed as two-component systems. They also use primary dyes as in permanent hair colorants but differ in that they use other alkalizing agents than ammonia, in particular alkanolamines such as monoethanolamine (MEA) or aminomethylpropanol (AMP), and usually function at lower concentration of hydrogen peroxide, typically 1 to 3 weight % (w. %) in the mixed product (also referred to as "on-head" composition) compared to 3 to 6 or even higher w. % for permanent "Level 3" colorants. Higher level of hydrogen peroxide are however sometime used when higher level of coloring are sought (up to 8% $H_2O_2$ on head for some shade). Other peroxides may also be used for Level 3 bleaching composition, e.g. persulfate, as oxidizing agent. Demi-permanent hair colorants usually cause less melanin bleaching and thus less lift (i.e. removal) of natural hair color. The resulting dyes also penetrate less deeply in the hair shaft so that demi-permanent hair colorants can be less stable than permanent hair colorants. On the other hand, demi-permanent hair colorants are usually also less damaging to the hair structure than permanent hair colorants and the resulting hair color may also be more natural looking. A further advantage is that demi-permanent hair colorant compositions do not have the strong ammonia smell of permanent hair colorant and thus have a better consumer acceptance. A professional brand of demi-permanent dyes in Europe is for example Color Touch® from Wella.

Ammonia-free hair coloring products have been proposed with the goal to provide coloring results close to those obtained with permanent dyes containing ammonia. For example Schwarzkopf has launched in 2009 in Germany a two-component ammonia-free colorant product under the brand name Essensity. The alkalizing agent used is MEA and relatively high level of hydrogen peroxide is used (up to 7.7% on head).

L'Oreal has launched in 2009 in Western Europe a three-component system for professional usage under the brand name INOA. The INOA products comprise a fatty component, a concentrated dye component and an oxidizing component to be mixed immediately before use. The fatty component comprises primarily mineral oil and does not comprise an alkalizing agent. The dye component comprises MEA as alkalizing agent. The 3 components are recommended to be mixed in a 40:16:60 weight ratio.

Several L'Oreal published patent documents disclose compositions more or less related to the INOA products. For example, US2010/0154141A1 assigned to L'Oreal discloses a process for coloring keratin materials comprising: applying to said keratin materials a coloring composition comprising a direct emulsion (A) comprising at least one fatty substance other than fatty acids present in an amount greater than 25% by weight; at least one surfactant; at least one alkaline agent; at least one colored or coloring entity chosen from direct dyes and oxidation dyes; and water in an amount greater than 5% by weight relative to the total weight of the direct emulsion (A); and a composition (B) comprising at least one oxidizing agent. The alkanolamine is preferably chosen from 2-amino-2-methyl-1-propanol and monoethanolamine.

US2010/0223739A2 assigned to L'Oreal discloses a process and kit for coloring or dyeing keratin fibers, in which the following are applied to the fibers: an aqueous cosmetic composition (A) comprising at least one fatty substance and at least one surfactant; a cosmetic composition (B) comprising at least one alkaline agent, a cosmetic composition (C) comprising at least one oxidizing agent, wherein the amount of the at least one fatty substance in composition (A) is greater than 20% by weight relative to the total weight of composition (A), and when the process used is a process for dyeing keratin fibers, then cosmetic composition (B) further comprises at least one oxidation dye, at least one direct dye, or both.

Further patent applications assigned to L'Oreal disclose coloring compositions obtained by mixing three components. For example US2009/0191142 discloses a process for dyeing human keratin fibers in the presence of at least one oxidizing agent, comprising applying to the fibers at least one anhydrous composition (A) comprising at least one fatty substance and at least one surfactant, at least one composition (B) comprising at least one oxidizing agent, and at least one composition (C) comprising at least one dye chosen from direct and oxidation dyes, and at least one organic amine having a pKb at 25° C. of less than 12. The disclosure also relates to a multi-compartment device containing, in separate compartments, the compositions (A), (B), and (C); and a method of making a ready-to-use composition. The present disclosure also relates to an anhydrous composition comprising at least one fatty substance, at least one surfactant, at least one dye, and at least one organic amine. L'Oreal's US2009/0162309, US2009/0158533, US2010/0175705, US2010/0175706, US2010/0178264, US2010/0154137 also disclose 3 components coloring compositions.

US2008/0052841A1 assigned to LES PRODUITS VERNICO LTEE discloses a method for permanently modifying a color of keratinous fibers with a mixture of three compositions A, B and C, wherein said composition A comprises at least a reducing agent and optionally a coloring compound, said composition B comprises at least an alkalizing compound and said composition C comprises at least an oxidizing compound.

U.S. Pat. No. 6,423,101, assigned to EUGENE PERMA discloses an ammonia-free composition for dyeing keratinous fibers, comprising an oxidant compound, coloring agent precursors and a non-volatile odorless alkalizing agent characterized in that it further comprises: a quaternized copolymer of dimethyldiallyl ammonium and acrylic acid; a quaternized silicone; and an acrylic-itaconic copolymer esterified with one or several fatty alcohol's, optionally polyoxyethylenated. The composition is prepared using a two-component system with MEA as alkalizing agent. According to this Patent, the specific ternary complex claimed provides coloration which gives good coverage and resistance similar to coloration using ammonia.

Although the prior art discloses using two- or three-component systems to obtain a permanent hair coloring result without ammonia, this has usually been obtained by the use of higher level of hydrogen peroxide, which can result in relatively higher damages to the hair fibers, especially after repeated treatments. Furthermore, the prior art has not provided a versatile system for providing different level of lift at the discretion of the user based a single tint component.

The present inventors have now surprisingly found that it was possible to formulate high lift coloring compositions based on a non-ammonia alkalizing agent while keeping hair damage to acceptable level. The inventors have found that increasing the weight ratio of the non-ammonia alkalizing agent to hydrogen peroxide provided improved results. This increased ratio can be obtained using a two-component system, in which case the tint component may be provided with higher than usual level of non-ammonia alkalizing agent. The inventors have also found that the lift provided by typical two-component demi-permanent coloring products can be increased by mixing them with a third component comprising a non-ammonia alkalizing agent, while keeping the damage at acceptable level. The compositions of the invention can provide similar level of lift and/or intensity of coloration but at lower hair fiber damage level than compositions with higher level of hydrogen peroxide.

SUMMARY OF THE INVENTION

The present invention is for an oxidative hair coloring composition comprising, by weight of the composition:
- at least 1.5% of a non-ammonia alkalizing agent selected from the group consisting of monoethanolamine, diethanolamine, triethanolamine, monopropanolamine, dipropanolamine, tripropanolamine, 2-amino-2-methyl-1,3-propanediol, 2-amino-2-methyl-1-propanol, 2-amino-2-hydroxymethyl-1,3-propanediol and mixtures thereof;
- from 0.5% to 4% of hydrogen peroxide;
- oxidative primary dyes;

wherein the weight ratio of said non-ammonia alkalizing agent to hydrogen peroxide is higher than or equal to 1.10.

Compositions comprising in combination a quaternized copolymer of dimethyldiallylammonium and acrylic acid, a quaternized silicone, and an acrylate-itaconate copolymer esterified with at least one fatty alcohol are excluded from the scope of this invention.

The non-ammonia alkalizing agent may in particular be monoethanolamine. The compositions may comprise low level of ammonia or preferably no ammonia at all. These preferred features as well as other preferred but non-limiting features of the present invention are further disclosed in the following description and claims.

The invention is also for a method for preparing the compositions of the invention comprising the step of mixing two or optionally three components.

DETAILED DESCRIPTION OF THE INVENTION

Definitions

By "oxidative hair coloring composition", it is meant a ready-to-use composition which can change the color of hair on which it is applied and which comprises an alkalizing agent, an oxidizing agent and oxidative primary dyes. By "two-component" oxidative hair coloring composition it is meant an oxidative hair coloring composition which is obtained by mixing shortly before use two components: a tint component and an oxidizing component. The tint component comprises the oxidative primary dyes and the alkalizing agent. The oxidizing component comprises the oxidizing agent. By "component" it is meant an individual composition which is mixed by the user with one or more other components for preparing the ready-to-use oxidative hair coloring composition to be applied to the hair. By "user" it is meant the person preparing the hair coloring composition. The user may be for example a professional hair stylist working in a salon and thus a different person than the one on which hair the composition is applied, or the user may be the same person as the one to which the hair belongs.

By "lift" (or "lift power") it is meant the amount of removal of the natural hair pigment that the coloring composition can provide. The amount of lift provided by different hair coloring compositions can be compared using human natural dark hair sample (e.g. hair of individual of Chinese descent) and measuring the change of color achieved following application of the compositions. The change in color can be measured using well known parameters such as $L^*a^*b^*$ values. A composition can be said to provide a higher lift than another composition when the $\Delta L^*$ value measured for a given treated sample of dark hair is higher for that composition than for the other composition, using the same experimental condition of course. The denomination Level 2 (herein used interchangeably with "demi-permanent" or "tone-on-tone") and Level 3 (herein used interchangeably with "permanent") are commonly used in the hair care trade to differentiate compositions with medium and high lift, although there is no official definition for differentiating a Level 2 from a Level 3.

By "oxidizing agent" it is meant an electron accepting compound suitable for use in hair coloring compositions for removing the natural color of hair (by destroying the melanin pigment) and reacting with oxidative primary dyes to provide an oxidative hair color. The most commonly used oxidizing agent in the art is hydrogen peroxide, however further suitable oxidizing agents that can be used in combination with hydrogen peroxide will be described below.

By "alkalizing agent" it is meant one or more compounds suitable for raising the pH to alkaline level in hair coloring compositions, in particular to a pH between 9 and 11. Generally, the most commonly used alkalizing agent in the art is ammonia, however the present invention involves using alkalizing agent other than ammonia (herein "non-ammonia" alkalizing agent), in particular alkanolamines such as monoethanolamine. Alternative non-ammonia alkalizing agents will be described below.

Herein, "comprising" means that other steps and other ingredients can be added to the term qualified. On the other hand, the term "consisting of" means that other steps and other ingredients (other than trace amount) are excluded.

All percentages are by weight of the ready-to-use coloring composition (i.e. as applied on head after the two or more components have been mixed) unless specifically stated otherwise. All ratios are weight ratios unless specifically stated otherwise.

Non-Ammonia Alkalizing Agent

The compositions of the invention comprise a non-ammonia alkalizing agent selected from the group consisting of monoethanolamine (MEA), diethanolamine, triethanolamine, monopropanolamine, dipropanolamine, tripropanolamine, 2-amino-2-methyl-1,3-propanediol, 2-amino-2-methyl-1-propanol (a.k.a. aminomethylpropanol, AMP), 2-amino-2-hydroxymethyl-1,3-propanediol and mixtures thereof.

Monoethanolamine (MEA) or aminomethylpropanol (AMP) are commonly used in ammonia-free hair dye products and may be preferred as alkalizing agent alone or in combination with each other or other alkalizing agents. Monoethanolamine may be in particular be preferred to be used alone or in combination with other non-ammonia alkalizing agent.

Although the compositions of the invention may comprise in some embodiments some amount of ammonia in addition to the non-ammonia alkalizing agent, for example less than 0.5% ammonia, it is preferred that the hair coloring composition of the invention is free of ammonia.

Oxidizing Agent

The composition of the invention comprises from 0.5% to 4% by weight of hydrogen peroxide as oxidizing agent. Additional oxidizing agent may also be present such as sodium periodate, urea peroxide, melamine peroxide, perborates, percarbonates, perphosphates, persilicates, persulphates, peroxidises and mixtures thereof, but it may be preferred to use only hydrogen peroxide.

As will be demonstrated in the Experimental section below, the inventors have found that the weight ratio of the non-ammonia alkalizing agent to hydrogen peroxide should be higher or equal to 1.10, preferably from 1.10 to 4.0, more preferably of from 1.20 to 3.0. The inventors believe that this ratio provides unexpected high lift with relatively low hair damage. Until the invention, it was generally thought that the lift power of a composition was driven by the concentration of oxidizing agent. However, it is also known that raising the concentration of oxidizing agent on-head can also increase the damage caused to the structure of hair fiber. The inventors now believe that it is in fact possible to increase the lift power of a composition by increasing the relative concentration of non-ammonia alkalizing agent relative to the concentration of oxidizing agent. In addition, the inventors have found that damages are kept in this way at relatively low level, and that for coloring composition the raise of the alkalizing agent concentration in the composition does not cause substantial color shift.

Method of Making

In one embodiment, the composition of the invention may be obtained by mixing two components, a tint component comprising the non-ammonia alkalizing agent and oxidative primary dyes, and an oxidizing component comprising the hydrogen peroxide. Such two components systems are commonly used in the art and each component is formulated so that the resulting mixture is a composition according to the invention.

In another embodiment, the composition of the invention may be obtained by mixing, in any order, three or more components:

a tint component, comprising a first non-ammonia alkalizing agent, and an oxidizing component comprising hydrogen peroxide, and a third component comprising a second non-ammonia alkalizing agent.

This method is advantageous because it leaves the user with the choice of using the third component or not. The inventors have found that by using such a third component, which raises the concentration of non-ammonia alkalizing agent in the composition, more lift can be obtained compared to the mixture of the tint component and oxidizing component only.

In such a method, the tint component and third component may preferably comprise the same non-ammonia alkalizing agent, in particular monoethanolamine. The concentration of the second alkalizing agent in the third component may also be higher than the concentration of the first alkalizing agent in the tint component so that the concentration in non-ammonia alkalizing agent is higher in the ready-to-use composition after the third component has been added (this is particular true when the three components are mixed in 1:1:1 ratio).

The concentration in non-ammonia alkalizing agent, in particular MEA, in the third component may be comprised between 3% and 15%, preferably 6% to 12%, more preferably 8% to 10% by weight of the third component, exemplarily 9% and is preferably higher than in the tint component. A relatively high concentration is believed to be necessary to raise the concentration in non-ammonia alkalizing agent in the final composition after mixing. The concentration in the first non-ammonia alkalizing agent in a tint component may for example be from 1.5% to 5% in the tint component.

The third component may be based on a similar chassis as the tint component to ease mixing but this is not required. For example, the tint component and third component may be oil-in-water emulsion. The second non-ammonia alkalizing agent may be the same or different than the first non-ammonia alkalizing agent.

The different components may be formulated in any usual cosmetic form, in particular oil-in-water emulsion. The oxidizing component may also be an oil-in-water emulsion or in other form for example a powder or an aqueous solution.

The different components may be mixed together in any order. When three components have to be mixed, they may be all mixed together or one after the other. For example the tint component and the oxidizing component may be mixed together, and the third component then added to this intermediate mixture.

A mixing ratio of 1:1:1 (by weight) for each component may be advantageous when a third component is used in one of the method steps of the invention. This 1:1:1 ratio allows the user to dose the different component in a simple way, as well as allow a simple calculation of the concentration of the oxidizing agent on-head. A concentration of 3% hydrogen peroxide on-head can for example be thus obtained by using a 9% concentrated hydrogen peroxide.

Formulation Chassis and Other Ingredients

The coloring compositions of the invention and the components used to make them can of course further comprise any usual chassis and use any common ingredients, known in the field as long as they are compatible with the requirements set in the claims. Common ingredients include but are not limited to: solvents; oxidative dyes; direct dyes; oxidizing agents other than hydrogen peroxide; radical scavengers; thickeners and or rheology modifiers; chelants; pH modifiers and buffering agents; carbonate ion sources; peroxymonocarbonate ion sources; anionic, cationic, nonionic, amphoteric or zwitterionic surfactants, or mixtures thereof; anionic, cationic, nonionic, amphoteric or zwitterionic polymers, or mixtures thereof; fragrances; enzymes; dispersing agents; peroxide stabilizing agents; antioxidants; natural ingredients, e.g. proteins and protein derivatives, and plant extracts; conditioning agents including silicones and cationic polymers, ceramides, preserving agents; and opacifiers and pearling agents (such as titanium dioxide and mica). Some adjuvants referred to above, but not specifically described below, which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose.

The following are only a few examples, which should be not be considered as limiting, and using other common elements or formulation chassis with the invention is of course possible.

Examples of formulation chassis for the tint component can be found for example in patent literature or adapted from existing commercial products, especially products comprising non-ammonia alkalizing agent such as from the Color-Touch® range marketed by Wella, Inoa® range marketed by L'Oreal or Essensity® range marketed by Schwarzkopf. The components may for example be formulated and delivered as aqueous hair product, emulsion, gel, aerosol, or foam.

A creamy carrier for the tint component (or third component if used) comprising (A) 10 to 30 w. % of at least one fatty alcohol with 10 to 24 carbon atoms; and one or more or preferably all of: (B) 0.2 to 6.0 w. % of at least one diester of formula: $R^1$—CO—O—$(CH_2$—$CH_2$—O$)_n$—CO—$R^2$, where n is 1, 2 or 3, and $R^1$ and $R^2$ are the same or different alkyl radicals with 12 to 20 carbon atoms; (C) 0.5 to 20 w. % glycerine fatty acid ester with 10 to 24 carbon atoms; (D) 0.1 to 10 w. % of non-ionic and/or anionic and/or ampholytic emulsifiers, in relation to the total weight of this tint component, and (E) has a pH of 4.5 to 12.5, may be used, as is for example disclosed in EP594,811A1. Lower level of fatty alcohol can also be used in this chassis if a less thick composition is desired, for example level of from 2% of at least one fatty alcohol with 10 to 24 carbon atoms.

The formulations disclosed in WO98/11863A2 may also be used. The formulations disclosed in this document contain a beeswax-protein hydrolysate-and/or amino acid association, which however may or may be not present in the tint component of the present invention.

The invention may also be put in practice with a three-component system, for example as disclosed in L'Oreal's US2010/0223739A2, in which case the aqueous cosmetic composition (A) comprising at least one fatty substance and at least one surfactant as defined in this document may be considered as a fourth composition.

The oxidizing component (and the third component if used) may be based on the same or similar (i.e. having the same ingredients but possibly at different level) formulation chassis as the tint component, but these components are normally free of oxidative dye precursors or direct dyes.

Among the usual ingredients encountered in coloring compositions, the presence of a chelant such as EDTA or EDDS may be beneficial in several ways, as it was shown that chelants can reduce hair damage due to the oxidizing agent (see WO02/089754, in particular the chelants listed on page 14 line 26 to page 17 line 5, especially EDDS). Chelants, usually disodium EDTA, are also commonly used as stabilizer in the oxidizing component.

Among oxidative primary dyes, common primary intermediates are for example toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-didhydroxyethyl)-p-phenylenediamine, 2-chloro-p-phenylenediamine, p-aminophenol, p-methylaminophenol, 4-amino-m-cresol, 6-amino-m-cresol, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate.

Commonly used couplers are for example resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylamino-phenol, 3-amino-2,6-dimethylphenol, 3-amino-2,4-dichlorphenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylamino-anisole, 1,3-bis-(2,4-diaminophenoxy)-propane, 2,6-dihydroxyethylamino-toluene, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol, 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline). These and other primary intermediates and couplers may be used in different combination to achieve the nuance sought, as is known in the art.

Direct dyes may also be incorporated in any of components of the invention, in particular the tint component. The compositions of the present invention may also comprise compatible direct dyes, in an amount sufficient to provide additional coloring, particularly with regard to intensity. Typically, such an amount will range from 0.05% to 4%, by weight, of the composition. When the composition is obtained by mixing a tint component and an oxidizing component, the direct dyes are usually incorporated in the tint component.

The following direct dyes are commonly used: Acid dyes such as Acid Yellow 1, Acid Orange 3, Acid Black 1, Acid Black 52, Acid Orange 7, Acid Red 33, Acid Yellow 23, Acid Blue 9, Acid Violet 43, Acid Blue 62, Acid Blue 25, Acid Red 4, Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)

phenyl)diazenyl)-1-methyl-1H-imidazol-3-ium-3-yl)
butane-1-sulfonate, (E)-4-(4-(2-methyl-2-phenylhydrazono)
methyl)pyridinium-1-yl)butane-1-sulfonate, N,N-dimethyl-
3-(4-(methylamino)-9,10-dioxo-4-a,9,9a,10-
tetrahydroanthracen-1-ylamino)-N-propylpropan-1-
aminium bromide, Disperse Dyes such as Disperse Red 17,
Disperse Violet 1, Disperse Red 15, Disperse Violet 1, Disperse Black 9, Disperse Blue 3, Disperse Blue 23, Disperse
Blue 377, Nitro Dyes such as 1-(2-(4-nitrophenylamino)
ethyl)urea, 2-(4-methyl-2-nitrophenylamino)ethanol, 4-nitrobenzene-1,2-diamine, 2-nitrobenzene-1,4-diamine,
Picramic acid, HC Red No. 13, 2,2'-(2-nitro-1,4-phenylene)
bis(azanediyl)diethanol, HC Yellow No. 5, HC Red No. 7, HC
Blue No. 2, HC Yellow No. 4, HC Yellow No. 2, HC Orange
No. 1, HC Red No. 1,2-(4-amino-2-chloro-5-nitrophenylamino)ethanol, HC Red No. 3,4-amino-3-nitrophenol, 4-(2-hydroxyethylamino)-3-nitrophenol, 2-amino-3-nitrophenol,
2-(3-(methylamino)-4-nitrophenoxy)ethanol, 3-(3-amino-4-nitrophenyl)propane-1,2-diol, HC Yellow No. 11, HC Violet
No. 1, HC Orange No. 2, HC Orange No. 3, HC Yellow No. 9,
HC Red No. 10, HC Red No. 11, 2-(2-hydroxyethylamino)-
4,6-dinitrophenol, HC Blue No. 12, HC Yellow No. 6, HC
Yellow No. 12, HC Blue No. 10, HC Yellow No. 7, HC Yellow
No. 10, HC Blue No. 9,2-chloro-6-(ethylamino)-4-nitrophenol, 6-nitropyridine-2,5-diamine, HC Violet No. 2,2-amino-
6-chloro-4-nitrophenol, 4-(3-hydroxypropylamino)-3-nitrophenol, HC Yellow No. 13,6-nitro-1,2,3,4-
tetrahydroquinoxaline, HC Red No. 14, HC Yellow No. 15,
HC Yellow No. 14, N2-methyl-6-nitropyridine-2,5-diamine,
N1-allyl-2-nitrobenzene-1,4-diamine, HC Red No. 8, HC
Green No. 1, HC Blue No. 14, and Natural dyes such as
Annato, Anthocyanin, Beetroot, Carotene, Capsanthin, Lycopene, Chlorophyll, Henna, Indigo, Cochineal.

The coloring compositions of the invention and any of the components used in the invention may comprise a thickener, in particular a polymeric thickener in an amount sufficient to provide the composition with a viscosity so that it can be readily applied to the hair without unduly dripping off the hair, as is known in the art. Typically, such an amount will be at least about 0.1%, in some embodiments, at least about 0.5%, in other embodiments, at least about 1%, by weight of the composition. Examples of commonly used associative polymeric thickeners are sold under the tradename Aculyn-22 by the company Rohm & Haas, Permulen TR1, Carbopol 2020, Carbopol Ultrez-21 by the company Noveon, and Structure 2001 and Structure 3001 by the company National Starch. Other suitable polymers include polyether polyurethanes, for example Aculyn-44 and Aculyn-46 by the company Rohm and Haas. Another suitable associative polymer is cellulose modified with groups comprising at least one C8-C30 fatty chain, such as the product Natrosol Plus Grade 330 CS sold by the company Aqualon.

Suitable non-associative cross-linked polycarboxylic polymers for use herein can be chosen, for example, from: (i) cross-linked acrylic acid homopolymers; or (ii) copolymers of acrylic or (meth)acrylic acid and of C1-C6 alkyl acrylate or (meth)acrylate. Such polymers are sold under the names Carbopol 980, 981, 954, 2984, 5984 by the company Noveon or Synthalen M, Synthalen L and Synthalen K by the company 3V Sigma, or Aculyn-33 by the company Rohm and Haas.

Polysaccharides may also be used, for example, glucans, modified and unmodified starches, amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, such as guar gums, and non-ionic derivatives thereof (hydroxypropyl guar) and biopolysaccharides, such as xanthan gums, gellan gums, welan gums, scleroglucans, succinoglycans and mixtures thereof. Suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums-Polysaccharides and their Derivatives", edited by Roy L. Whistler, Second Edition, published by Academic Press Inc.

Salt tolerant thickeners may also be advantageously used, including but not limited to: xanthan, guar, hydroxypropyl guar, scleroglucan, methyl cellulose, ethyl cellulose (available as AQUACOTE®), hydroxyethyl cellulose (NATROSOL®), carboxymethyl cellulose, hydroxypropylmethyl cellulose, microcrystalline cellulose, hydroxybutylmethyl cellulose, hydroxypropyl cellulose (available as KLUCEL®), hydroxyethyl ethyl cellulose, cetyl hydroxyethyl cellulose (available as NATROSOL® Plus 330), N-vinylpyrollidone (available as POVIDONE®), Acrylates/Ceteth-20 Itaconate Copolymer (available as STRUCTURE® 3001), hydroxypropyl starch phosphate (available as STRUCTURE® ZEA), polyethoxylated urethanes or polycarbamyl polyglycol ester (e.g. PEG-150/Decyl/SMDI copolymer (e.g. ACULYN® 44), PEG-150/Stearyl/SMDI copolymer (available as ACULYN® 46), trihydroxystearin (available as THIXCIN®), acrylates copolymer (e.g. available as ACULYN® 33) or hydrophobically modified acrylate copolymers (e.g. Acrylates/Steareth-20 Methacrylate Copolymer (available as ACULYN® 22), acrylates/steareth-20 methacrylate crosspolymer (available as ACULYN® 88), acrylates/vinyl neodecanoate crosspolymer (available as ACULYN® 38), acrylates/beheneth-25 methacrylate copolymer (available as ACULYN® 28), acrylates/C10-30 alkyl acrylate crosspolymer (available as Carbopol® ETD 2020), non-ionic amphophilic polymers comprising at least one fatty chain and at least one hydrophilic unit selected from polyether urethanes comprising at least one fatty chain, and blends of Ceteth-10 phosphate, Di-cetyl phosphate and Cetearyl alcohol (available as CRODAFOS® CES).

Compositions comprising in combination a quaternized copolymer of dimethyldiallylammonium and acrylic acid, a quaternized silicone, and an acrylate-itaconate copolymer esterified with at least one fatty alcohol (C12-C18) are excluded from the scope of this invention. It was found that such combinations as disclosed in U.S. Pat. No. 6,423,101 were not necessary to provide the benefits of the invention.

The components of the invention can be manufactured using any suitable standard processes known in the art.

Packaging

Before use, the different components used in the invention are normally packaged separately from one another. The components may be packaged separate primary packages such as plastic bottle or sachet. The components, in particular each component of a two-component composition, may however be packaged separately but within a common secondary package such as a carton or in different compartment of an aerosol or foam bottle, as in known in the trade. A conditioning composition, which can be applied after rinsing of the hair coloring composition, may also be packaged in such secondary package. On the other hand, the different components of the invention, in particular the third component, may be sold separately from the other components.

Method of Use

Application of the hair coloring composition to the hair may be undertaken in several ways. Application of the hair coloring composition may take place on the whole head of hair of an end user. As used herein, the "whole head of hair" means that the hair all over the head from the root of the hair to the tip of the hair is included in the application process. By contrast, the application of the hair coloring composition may take place on the root portion of the hair. The application to the root portion of the hair may still be over the entire head of the end user, but application of the hair coloring composition is applied only to the section of hair closest to the head (root portion), which is between about 0.01 mm to about 4 mm from the scalp of the head. Also, application may take place on a portion of hair. Application of a portion of hair is commonly referred to as highlighting or lowlighting. The portion of hair may be physically separated from the whole head of hair in a hair bundle or may be a smaller portion of hair than the whole head of hair. A hair bundle may be physically separated from a whole head of hair by a device including a plastic cap through which hair bundles are formed when hair is pulled through orifices in the plastic cap, metal foils encompassing a hair bundle, strand separators applied to hair at the root portion, or similar devices.

When present, an optional conditioning agent can be provided in an additional container. In the latter case, the conditioner can be mixed immediately before use and applied together with the other components, or the content of the additional container can be applied (after an optional rinse step) as a post-treatment immediately after the hair coloring composition.

According to one method for oxidatively coloring hair, the method comprises mixing a tint component and an oxidizing component and optionally a third component comprising a second non-ammonia alkalizing agent together to form a hair coloring composition, applying the hair coloring composition to the hair to form a treated hair surface, waiting for a period of 5-45 minutes, such as 20-30 minutes, and then removing the hair coloring composition from the treated hair surface.

The methods of coloring hair also may further comprise working the hair coloring composition into the treated hair surface by hand or by a tool for a few minutes to ensure uniform application to the entire treated hair surface. The hair coloring composition remains on the treated hair surface while the end hair color develops for a time period of 5 to 45 minutes to form oxidatively colored hair. The consumer then rinses his/her oxidatively colored hair thoroughly with tap water and allows it to dry and/or styles the oxidatively colored hair.

EXAMPLES

In the following, compositions according to the invention were tested for lift and hair damage and compared to currently marketed products. The following abbreviations are used in the Table below:

CT: ColorTouch® (a "Level 2" coloring composition with MEA as alkalizing agent) in particular the shade 10/0 ("CT10/0"). The INCI list and percentage weight range for CT10/0 are: (>10%:) Aqua, (1%-10%:) Cetearyl Alcohol, Ethanolamine, Sodium Sulfate, Laureth-3, Sodium Laureth Sulfate, Glyceryl Stearate SE, (0.1%-1%:) Decyltetradecanol, Sodium Lauryl Sulfate, Cera Alba, Parfum, Sodium Cocoyl Isethionate, Mica, Sodium Sulfite, Ascorbic Acid, Etidronic acid, Hydrolyzed Keratin, (<0.1%:) Colorant, Citric acid.

4% CT Emulsion: ColorTouch® Oxidizing Emulsion having 4% $H_2O_2$ concentration. The INCI list and percentage weight range for 4% CT Emulsion are (>10%:) Aqua, (1%-10%:) Hydrogen Peroxide, Cetearyl Alcohol, (0.1%-1%:) Lanolin Alcohol, Sodium Lauryl Sulfate, Parfum, Salicylic Acid, (<0.1%:) Disodium Phosphate, Phosphoric Acid, Etidronic Acid, Potassium Phosphate, Tocopherol.

6%, 9% Welloxon: Welloxon® Emulsion with respectively 6 and 9w. % $H_2O_2$, comprising as INCI ingredients; Aqua, Hydrogen Peroxide, Cetearyl Alcohol, Ceteareth-25, Salicylic Acid, Phosphoric Acid, Disodium Phosphate, Etidronic Acid.

KP: Koleston Perfect (a "Level 3" tint component with ammonia as alkalizing agent), in particular shade 10/0 ("KP10/0"). The INCI list and percentage weight range for KP10/0 are (>10%:) Aqua, Cetearyl Alcohol, (1-10%:) Glyceryl Stearate SE, Ammonium Hydroxide, Sodium Laureth Sulfate, Lanolin Alcohol, Sodium Lauryl Sulfate, Sodium Sulfate, Glycol Distearate, Sodium Cocoyl Isethionate, Sodium sulfite, Ascorbic Acid, Parfum, (<0.1%:), Disodium EDTA, Toluene-2,5-Diamine Sulfate, 2-Methylresorcinol, Citric Acid, Resorcinol, Tocopherol.

INOA: a "Level 3" tint component comprising MEA as alkalizing agent and marketed by L'Oreal as a three component system (Oleogel+Developer+Tint). INOA is a Trademark of L'Oreal. The shade number 10, closest equivalent to KP10/0 and CT10/0 was tested.

The third component ("Booster" in the Table below) according to the invention was an O/W emulsion with the following formula:

TABLE 1

| Ingredient | Percent |
| --- | --- |
| Ethanolamine | 9 |
| Cetearyl Alcohol (and) Sodium Lauryl Sulfate (90:10 ratio) | 7 |
| Sodium Sulfite | 4 |
| Laureth-3 | 3 |
| Glyceral Distearate SE | 2.2 |
| Decyltetradecanol | 0.8 |
| Beeswax | 0.5 |
| Perfume | 0.5 |
| Gleamer Flake | 0.5 |
| Sodium cocoyl isothianate | 0.2 |
| Water | q.s. |

The Booster is a relatively highly concentrated MEA-containing component which can be used to raise the concentration of MEA of other composition and thus the ratio of MEA/$H_2O_2$ of commercial compositions. However, the present invention is not limited to compositions obtained by mixing three components, for example when the tint component is already formulated with a high concentration of MEA so that a third component may not be necessary to obtain the claimed ratio of non-ammonia alkalizing agent to hydrogen peroxide.

In the following experiments, the CT tint component was mixed in the recommended 1:2 weight ratio with the oxidizing component if the third component ("Booster") was not used. The KP tint component was mixed in a 1:1 ratio with the oxidizing component to reflect usual practice. If the Booster was used to make a three components mix, then each component was mixed in a 1:1:1 ratio. The INOA product was prepared following L'Oreal's recommendation with a 6% hydrogen peroxide composition.

EXPERIMENTAL

In the experiment, the shade 10/0 (natural bright blond) was used for both KP and CT and the equivalent INOA shade number 10 from L'Oreal. After mixing the correspondent components, the resulting coloring compositions were applied on tresses of medium brown hair 1.4 cm wide, 13 cm long with a development time of 35 nm. The hair was then shampooed and conditioned with standard products. The experiments were conducted on two batches of hair and the values measured averaged.

The amount of lift obtained was then measured using a Konica/Minolta D 508 Colorimeter and characterized by the difference in L* value measured ($\Delta L^*$). The damage to the hair fibers was assessed for each sample by measuring the concentration of cysteic acid after one treatment. The cysteic unit measurement is highly reliable (standard deviation less than 3%) and was performed by DWI, an independent research institute affiliated to Aachen University in Germany. The concentration of cysteic acid is representative of the amount of damage to intermolecular bonds within the hair fibers. The cysteic acid concentration for the untreated sample laid by 45.84 µmol/g. The concentration in alkalizing agent and $H_2O_2$ and the measured $\Delta L^*$ and cysteic acid concentration values are summarized in the Table below. The second and third compositions tested are compositions according to the invention.

This experiment also shows that the third component ("Booster") can significantly increase the level of lift provided by an already marketed hair coloring composition comprising a non-ammonia alkalizing agent such ase MEA. For example comparing the first two compositions of the table, the lift ($\Delta L^*$) went from 3.37 for a composition without the Booster to 5.13 for a composition with the Booster even as the concentration in peroxide is lowered. Although not wishing to be bound by theory, the inventors hypothesize that this surprising effect may be caused by the raised level of non-ammonia alkalizing agent (MEA) and the resulting higher value for the MEA/$H_2O_2$ ratio.

Remark

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document

TABLE 2

| Composition tested | Mixing ratio of the components | w. % MEA or NH3 in the composition | w. % $H_2O_2$ in the composition | Ratio MEA/$H_2O_2$ | $\Delta L^*$ Std deviation +/− 0.50 | Cysteic acid (µmol/g) |
|---|---|---|---|---|---|---|
| CT10/0 + 4% CT Emulsion | 1:2 | 1.33 MEA | 2.7 | 0.49 | 3.37 | 61.19 |
| CT10/0 + Booster + 6% Welloxon | 1:1:1 | 4.33 MEA | 2 | 2.17 | 5.13 | 78.56 |
| CT10/0 + Booster + 9% Welloxon | 1:1:1 | 4.33 MEA | 3 | 1.44 | 6.44 | 77.31 |
| KP10/0 + 9% Welloxon | 1:1 | 1.02 NH3 | 4.5 | — | 7.02 | 80.00 |
| INOA 10 (Oleogel + Developer 9% $H_2O_2$ + Tint) | 40:60:16 | 2.3 MEA (estimated) | 4.7 | 0.49 (estimated) | 7.14 | 93.90 |

The compositions of the invention (second and third compositions tested) provide a relatively high lift ($\Delta L^*>5$), which is comparable with the lift obtained with a "Level 3" classic colorant (KP10/0) using $NH_3$ and with the lift provided by the high lift MEA-based product from L'Oreal (INOA 10).

The lift obtained with the compositions of the invention was also superior compared to current MEA based product such as CT10/0 even though the concentration in hydrogen peroxide was lower (compare first and second composition tested).

The damage as assessed using cysteic acid concentration for the compositions of the invention were similar to the damages measured for an ammonia based colorant, KP10/0, but on the other hand the cysteic acid concentration is significantly lower for the compositions of the invention than with currently marketed non-ammonia containing product (INOA).

conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oxidative hair coloring composition comprising, by weight of the composition:
    at least 1.5% of a non-ammonia alkalizing agent selected from the group consisting of monoethanolamine, diethanolamine, triethanolamine, monopropanolamine, dipropanolamine, tripropanolamine, 2-amino-2-methyl-1,3- propanediol, 2-amino-2-methyl-1-propanol, 2-amino-2-hydroxymethyl-1,3-propanediol and mixtures thereof;

from 0.5% to 4% of hydrogen peroxide; and oxidative primary dyes;

wherein the weight ratio of said non-ammonia alkalizing agent to hydrogen peroxide is higher than or equal to 1.10, with the proviso that the composition does not comprise a quaternized copolymer of dimethyldiallylammonium and acrylic acid, a quaternized silicone and an acrylate-itaconate copolymer esterified with at least one fatty alcohol.

2. A composition according to claim 1 wherein the weight ratio of said non-ammonia alkalizing agent to hydrogen peroxide is of from 1.10 to 4.0.

3. A composition according to claim 2 wherein the weight ratio of said non-ammonia alkalizing agent to hydrogen peroxide is of from 1.20 to 3.0.

4. A composition according to claim 1 further comprising direct dyes.

5. A composition according to claim 1 comprising less than 0.5% by weight of ammonia.

6. A composition according to claim 5 comprising no ammonia.

7. A composition according to claim 1 comprising from 1.5% to 8% of said non-ammonia alkalizing agent by weight of the composition.

8. A composition according to claim 7 comprising from 2.0% to 6% of said non-ammonia alkalizing agent by weight of the composition.

9. A composition according to claim 1 wherein said non-ammonia alkalizing agent comprises monoethanolamine.

10. A composition according to claim 9 wherein said non-ammonia alkalizing agent consists of monoethanolamine.

11. A method for making an oxidative hair coloring composition comprising the steps of mixing in any order:

a tint component comprising a first non-ammonia alkalizing agent and oxidative primary dyes, an oxidizing component comprising hydrogen peroxide, and optionally a third component comprising a second non-ammonia alkalizing agent, wherein the oxidative hair coloring composition obtained after mixing these components is according to claim 1.

12. A method according to claim 11 wherein the first non-ammonia alkalizing agent and, when present, the second non-ammonia alkalizing agent are selected from the group consisting of monoethanolamine, diethanolamine, triethanolamine, monopropanolamine, dipropanolamine, tripropanolamine, 2-amino-2-methyl-1,3-propanediol, 2-amino-2-methyl-1-propanol, 2-amino-2-hydroxymethyl-1,3-propanediol and mixtures thereof.

13. A method according to claim 12 wherein the first non-ammonia alkalizing agent and, when present the second non-ammonia alkalizing agent, consists of monoethanolamine.

14. A method according to claim 11 wherein a second non-ammonia alkalizing agent is used and wherein the concentration by weight of the first non-ammonia alkalizing agent in the tint component is higher than the concentration by weight of the second alkalizing agent in the third component.

* * * * *